(12) United States Patent
Chu et al.

(10) Patent No.: US 7,517,882 B2
(45) Date of Patent: Apr. 14, 2009

(54) PROTEIN KINASE INHIBITORS

(75) Inventors: Shaosong Chu, Encinitas, CA (US); Zhe Nie, San Diego, CA (US); Carin L. Perretta, Greenville, SC (US); Philip Eugene Erickson, San Diego, CA (US)

(73) Assignee: Polaris Group, Taipei, Taiwan (CN)

( * ) Notice: Subject to any disclaimer, the term of this patent is extended or adjusted under 35 U.S.C. 154(b) by 0 days.

(21) Appl. No.: 11/856,476

(22) Filed: Sep. 17, 2007

(65) Prior Publication Data

US 2008/0070893 A1    Mar. 20, 2008

Related U.S. Application Data

(60) Provisional application No. 60/845,314, filed on Sep. 18, 2006.

(51) Int. Cl.
*C07D 245/00* (2006.01)
*A61K 31/53* (2006.01)
*A61K 31/395* (2006.01)

(52) U.S. Cl. ............ 514/243; 514/269.3; 540/460
(58) Field of Classification Search ............ 540/460; 514/243, 259.3
See application file for complete search history.

(56) References Cited

U.S. PATENT DOCUMENTS

| 2007/0149481 A1 | 6/2007 | Monse et al. |
| 2007/0244132 A1 | 10/2007 | Ishikawa |

FOREIGN PATENT DOCUMENTS

| EP | 1752457 A1 | 2/2007 |
| WO | 2004/048384 A1 | 6/2004 |
| WO | 2004/104007 A1 | 12/2004 |

*Primary Examiner*—Bruck Kifle
(74) *Attorney, Agent, or Firm*—Woodcock Washburn LLP

(57) ABSTRACT

Pyrimidine- and triazine-based chemical compounds that are useful, for example, as protein kinase inhibitors for treating cancer, neurological disorders, autoimmune disorders, and other diseases, and methods of using such compounds.

14 Claims, No Drawings

PROTEIN KINASE INHIBITORS

CROSS-REFERENCE TO RELATED APPLICATIONS

This application claims benefit under 35 U.S.C. §119(e) of provisional U.S. patent application No. 60/845,314 filed Sep. 18, 2006.

The Contents of the above-referenced patent applications is herein incorporated by reference in its entirety.

FIELD OF THE INVENTION

The present invention relates to chemical compounds that are useful, for example, as protein kinase inhibitors for treating cancer, neurological disorders, autoimmune disorders, and other diseases, and methods of using such compounds.

BACKGROUND OF THE INVENTION

Homeostasis requires signaling between cells to coordinate activities such as cellular proliferation and differentiation. Inappropriate signaling can cause or exacerbate immune system pathologies, such as allergies, autoimmune diseases, and inflammation, as well as neurological and cardiovascular maladies. In particular, cancer, the uncontrolled proliferation of cells, is strongly associated with breakdown in normal cellular signaling. Signaling often involves catalyzed transfer of phosphoryl groups to and from serine, threonine, and tyrosine residues on proteins as part of signal transduction, a step catalyzed by enzymes called protein kinases. For this reason, efforts to treat cancer and other diseases have directed attention to inhibition of protein kinases.

CK2, an essential serine/threonine protein kinase, until recently has not been considered as a possible target in cancer chemotherapy, but a wide variety of cancers exhibit elevated levels of CK2 activity that correlate with the aggressiveness of tumor growth. Furthermore, decreasing CK2 activity, through use of small molecules, dominant negative overexpression of kinase inactive mutants, anti-sense methods, or small interfering RNAs, decreases cellular proliferation, increases the level of apoptosis in cancer cells, and eradicates the PC3 human prostate cancer cells from tumor-bearing mice. Existing C2 inhibitors such as emodin, coumarins, TBB (triazole), quinazolines, DRB and quercetin, however, while useful for laboratory studies, lack the qualities of a clinically useful chemotherapeutic agent.

A need remains, therefore, for compounds that inhibit CK2 activity for treating pathologies associated with phosphorylation catalyzed by this protein kinase.

SUMMARY OF THE INVENTION

One aspect of the present invention provides a new class of protein kinase inhibitors based upon macrocyclic pyrazolo[1,5-a][1,3,5]triazine and pyrazolo[1,5-a]pyrimidine compounds, methods of using them, pharmaceutically acceptable prodrugs, pharmaceutically active metabolites, and pharmaceutically acceptable salts thereof. Such compounds, prodrugs, metabolites, polymorphs, and pharmaceutically acceptable salts thereof are collectively referred to as "agents."

The invention also relates to pharmaceutical compositions comprising an effective amount of an agent with one or more pharmaceutically acceptable carriers.

Thus, the inventive agents and pharmaceutical compositions containing such agents are useful in treating various diseases including but not limited to those associated with uncontrolled or un-wanted cellular proliferation such as cancer, autoimmune diseases, viral diseases, fungal diseases, neurodegenerative disorders and cardiovascular diseases.

Preferred agents modulate and/or inhibit the activity of CK2 protein kinase. Thus, the pharmaceutical compositions containing such agents are useful in treating diseases mediated by kinase activity, such as cancer.

The invention relates generally to compounds of Formula (I), as well as prodrugs, pharmaceutically active metabolites, polymorphs, and pharmaceutically acceptable salts thereof:

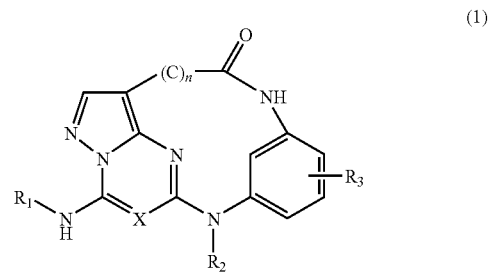

(1)

wherein
R1 is alkyl, alkenyl, alkynyl, aryl, or heteroaryl.
R2 is hydrogen, alkyl, alkenyl, alkynyl, aryl, or heteroaryl;
R3 groups are independently hydrogen, optionally substituted alkyl, alkenyl, alkynyl, aryl, heteroaryl, or halo:
(C) is a group selected from optionally substituted alkyl, alkenyl and alkynyl where n=2-6
X is CH or N.

The invention also relates to methods of treating proliferative diseases such as cancer, auto immune diseases, viral diseases, fungal diseases, neurodegenerative disorders and cardiovascular diseases, comprising administration of effective amounts of an agent of the invention to a subject in need of such treatment.

The invention further relates to methods of modulating and/or inhibiting the protein kinase activity of CK2 by administering a compound of Formula (I) or a pharmaceutically acceptable salt, pharmaceutically acceptable prodrug, or pharmaceutically acceptable salt of such compound or metabolite thereof.

DETAILED DESCRIPTION OF THE INVENTION

Unless otherwise specified, technical terms here take their usual meanings, specifically those specified in the McGraw-Hill Dictionary of Scientific and Technical Terms, 6th edition.

"Alkyl" refers to straight or branched hydrocarbon chains containing from 1 to 8 carbon atoms, while "alkylene" and "alkynyl" refer to the corresponding chains containing a double- or triple bond, respectively. Alkyl, alkylene, and alkynyl groups may be optionally substituted with one or more substituents selected from the group consisting of mercapto, nitro, cyano, azido and halo.

"Heteroaryl" refers to 5- and 6-membered aromatic rings having one or more heteroatoms selected independently from N, O, and S.

In preferred embodiments of the invention, R1 is aryl, preferably substituted aryl, more preferably substituted phenyl. It has been found that compounds in which R1 is N-alkyl-N-alkylpyrrolidinyl-carbonyl-phenyl (e.g., N-methyl-N-(1-methyl-pyrrolidinyl)-carbonyl)-phenyl, as in compound 11g) or N-alkyl-N-alkylaminoalkyl (e.g., N-methyl-N-ethylaminoethyl, as in compound 11s) are particularly useful. In certain preferred compounds, each R2 and R3 group is hydrogen, (C) is alkyl, n=4, and/or X is N.

Pyrimidine-(X=C) and triazine-based (X=N) compounds of Formula (I) are useful, for example, for influencing the activity of protein kinases. More particularly, the compounds are useful as anti-proliferation agents, thus providing treatments for cancer or other diseases associated with cellular proliferation mediated by protein kinases.

The inventive agents may be prepared by synthetic schemes described below. Triazine-based compounds of Formula (I), for example, can be prepared according to Scheme 1:

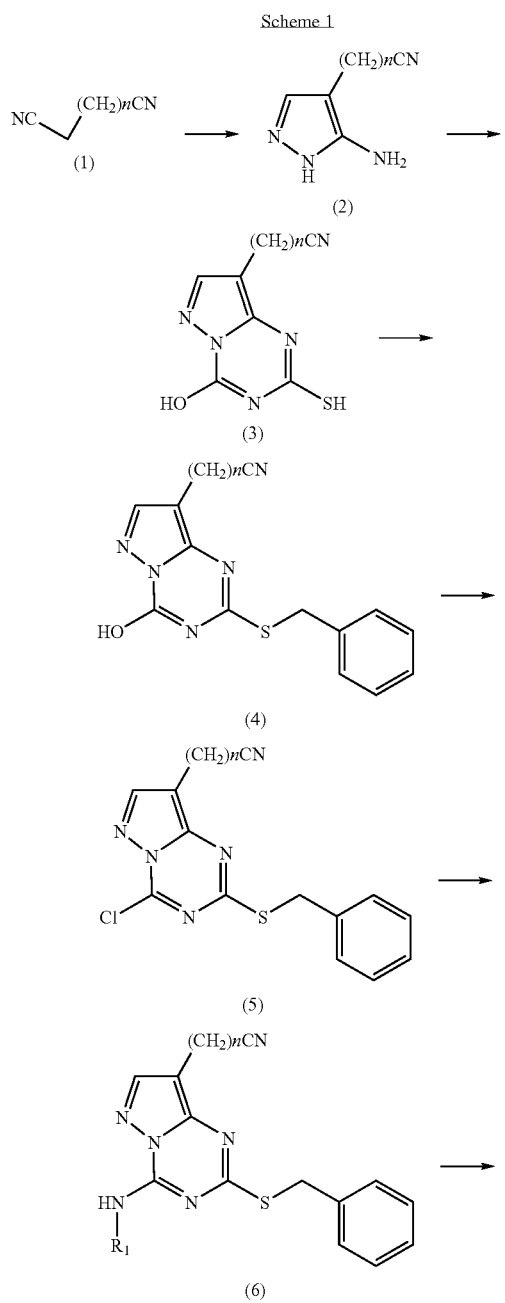

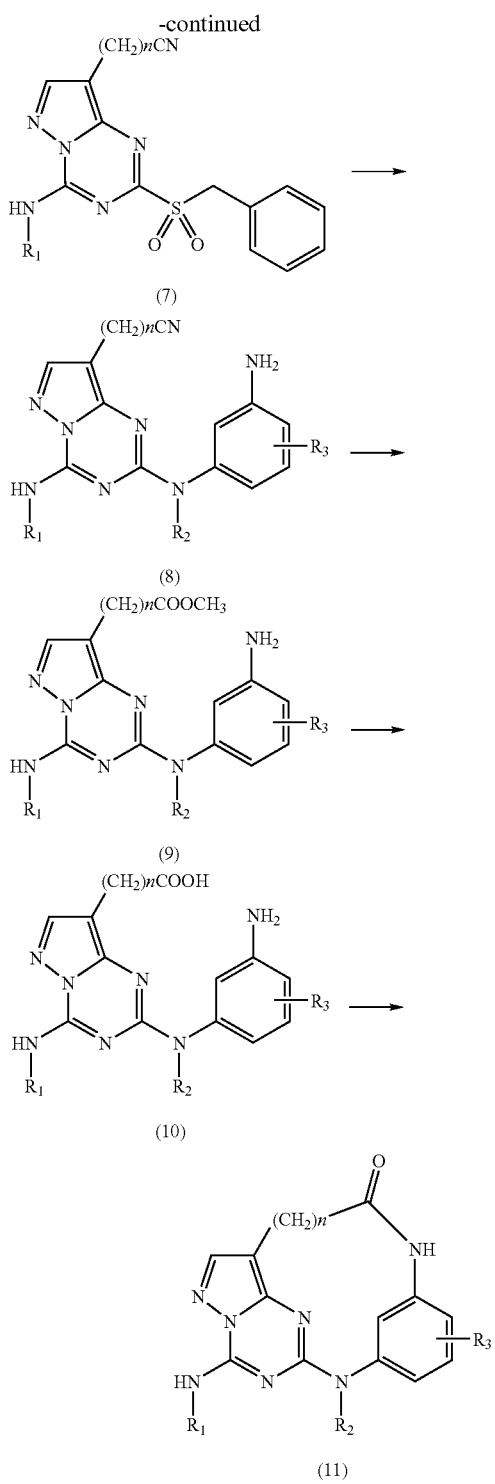

Synthesis of such compounds started from dicyano compounds (1). Treatment with NaH followed by ethylformate gave intermediate 2-formyl-dinitrile derivatives, which on treatment with hydrazine cyclized to provide 4-substituted amino pyrazoles (2). Compounds (2) were then treated with ethoxycarbonylisothiocyanate to form thiourea intermediates that spontaneously cyclize under basic conditions to provide compounds (3).

Benzylation followed by chlorination of compounds (3) gives corresponding compounds (4) and (5). The chloro group of compounds (5) was then replaced by a primary amine under mild condition to provide (6). Treatment of compounds (6) with mCPBA oxidized the benzylsulfanyl groups to the corresponding benzylsulfonyl ones (7). The activated benzylsulfonyl group of com-pounds (7) was then displaced by phenyl diamines to form compounds (8).

Treatment of compounds (8) with HCl gas in methanol gave compounds (9), which upon hydrolysis in basic conditions afforded compounds (10). Treatment of compounds (10) with coupling reagents afforded the desired macrocyclic compounds (11).

In a similar manner, pyrimidine-based (X=CH) compounds of Formula (I) were prepared ac-cording to Scheme 2:

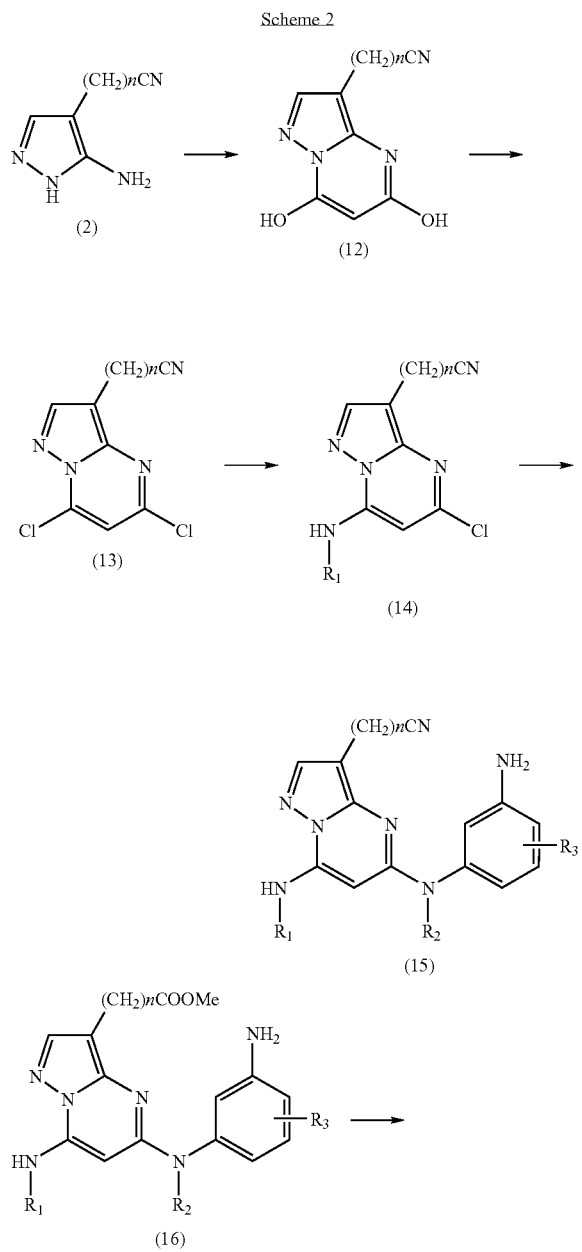

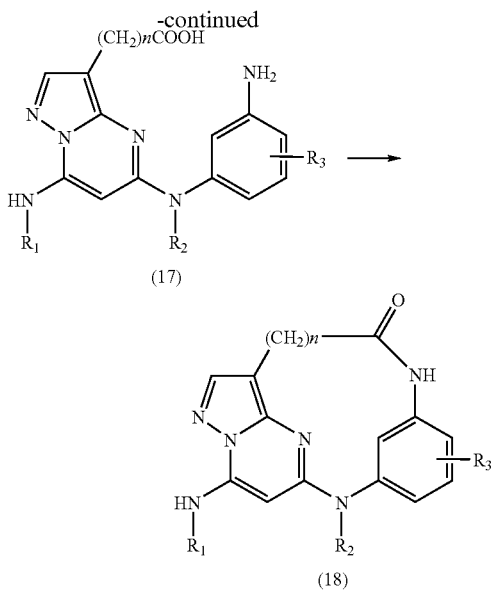

4-Substituted amino pyrazole (2) was first treated with chlorocarbonyl-acetic acid ethyl ester to give the diacylated intermediates, which were then cyclized in the presence of base to compounds (12). Dichlorination gave compounds (13), after which amine displacements provided compounds (14 and 15). Treatment of compounds (15) with HCl gas in methanol and refluxing in methanol gave compounds (16). Alkaline hydrolysis gave compounds (17) and macrocyclization afforded final product (18).

Pharmaceutically acceptable salts and/or solvates of compounds of the present invention may also be used. Such salts include those formed from, for example, hydrochloric, hydrobromic, sulfuric, phosphoric, nitric, fumaric, acetic, propionic, succinic, glycolic, maleic, tartaric, citric, malonic, and methanesulfonic acids.

Certain compounds may include a chiral center, in which case each enantiomer as well as the corresponding racemate is encompassed in the present invention.

The present invention also is directed to pharmaceutical formulations that include the inventive compounds, regardless of the intended mode of administration.

Therapeutic dosages of compounds of the present inventions can be readily determined by methods well-known in the art.

EXAMPLES

In the examples described below, unless otherwise indicated, all parts and percentages are by weight. Reagents were purchased from commercial suppliers such as Aldrich Chemical Company or Lancaster Synthesis, and were used without further purification unless otherwise indicated.

The reactions set forth below were done generally under a positive pressure of nitrogen or with drying tube, at ambient temperature (unless otherwise stated), in anhydrous solvents, and the re-action flasks were fitted with rubber septa for the introduction of substrates and reagents via syringe. The reactions were assayed by TLC, HPLC, LC/MS or NMR and terminated as judged by the consumption of starting material.

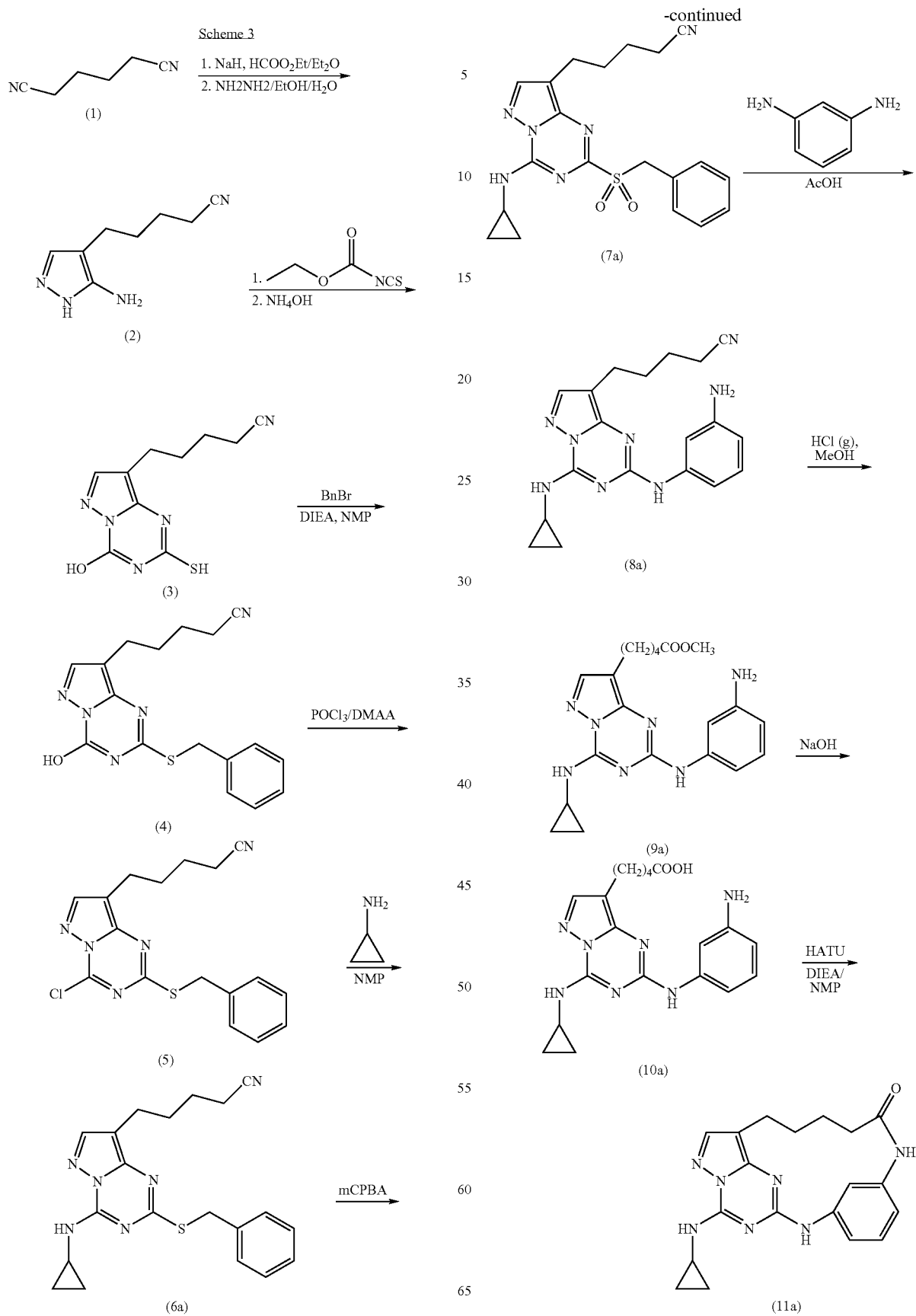

Example 1

5-(5-Amino-1H-Pyrazol-4-YL)-Pentanenitrile (2)

To a solution of 1,5-dicyanopentane (1) (6.5 mL, 50 mmol) and ethyl formate (20 mL, 250 mmol) in dry diethyl ether (200 mL), sodium hydride (60%, 4 g. 100 mmol) was added. The re-action mixture was refluxed for four h, cooled to room temperature filtered and rinsed with ether and dried. To a solution of above obtained white solid in 80% ethanol/water was added hydrazine hydrochloride (6.29 g. 61 mmol). The reaction mixture was adjusted to pH 3 with concentrated HCl and then refluxed for 2 h, cooled to room temperature and neutralized with NaHCO3. Solvent was removed under reduced pressure and the residue was dried in vacuum. The residue was suspended in ethanol and filtered. The filtrate was concentrated, dissolved in 5% MeOH/CH2Cl2, filtered through a short silica gel column, rinsed with 5% MeOH/CH2Cl2 and concentrated to give 5-(5-amino-1H-pyrazol-4-yl)-pentanenitrile 2 as a oil.

LCMS(API-ES) m/z: 164.2, 165.1 [M+H+]; 163.1 [M−H+].

Example 2

5-(4-Hydroxy-2-Mercapto-Pyrazolo[1,5-A][1,3,5]Triazin-8-YL)-Pentanenitrile (3)

To a solution of compound (2) (4.6 g. 14 mmol) in EtOAc (50 mL) was added Ethoxycarbonyli-sothiocyanate (1.69 mL, 15 mmol) drop wise with stirring at ambient temperature. The reaction mixture was refluxed for 2 h, and cooled to room temperature. Ammonium hydroxide (10 mL) was added and the reaction mixture stirred at room temperature for 20 h. The reaction mixture was extracted twice with 1 M NaOH and the aqueous extractions were combined, acidified with concentrate HCl, and extracted twice with EtOAc. The combined organic extracts were dried with anhydrous Na2SO4 and concentrated to give 5-(4-hydroxy-2-mercapto-pyrazolo[1,5-a][1,3,5]triazin-8-yl)-pentanenitrile (3), as a white solid (2.5 g, 67%).

LCMS(API-ES) m/z: 249.3, 249.9 [M+H+]; 247.9 [M−H+].

Example 3

5-(2-Benzylsulfanyl-4-Hydroxy-Pyrazolo[1,5-A][1,3,5]Triazin-8-YL)-Pentanenitrile (4)

A solution of compound (3) (5.3 g, 21,3 mmol) in N-methylpyrrolidinone (30 mL) was degassed in vacuum for 5 min. Benzyl bromide (2.28 mL, 19. 1 mmol) and DIEA (4.4 mL, 25 mmol) were added and the reaction mixture was stirred at room temperature under vacuum for 30 min. Sol-vent was removed under reduced pressure and the residue was diluted with EtOAc. The acetate solution was washed with 1 M HCl followed by brine. Organic extract was dried over anhydrous Na2SO4, filtered, and concentrated. The residue was triturated in a mixture solvent of hexane, ether and EtOAc, and filtered to give 5-(2-benzylsulfanyl-4-hydroxy-pyrazolo[1,5-a][1,3,5]triazin-8-yl)-pentanenitrile (4) as a solid (6.0 g. 93%).

LCMS(API-ES) m/z: 339.4, 340.0 [M+H+]; 338.0 [M−H+].

Example 4

5-(2-Benzylsulfanyl-4-Chloro-Pyrazolol [1,5-A][1,3,5]Triazin-8-YL)-Pentanenitrile (5)

A solution of compound (4) (6.0 g, 17.7 mmol) and N,N-dimethylaniline (2.24 mL, 17.7 mmol) in phosphorus oxychloride (20 mL) was heated to reflux in a sealed tube for 1 h. Solvent was removed and the residue was dissolved in EtOAc (200 mL) and washed with saturated aqueous NaHCO3, dilute HCl, followed by brine, dried over anhydrous Na2SO4, filtered and concentrated to give 5-(2-benzylsulfanyl-4-chloro-pyrazolo[1,5-a][1,3,5]triazin-8-yl)-pentanenitrile (5), which was used directly for the next step.

LCMS(API-ES) m/z: 357.8. 358.0. 360.0 [M+H+].

Example 5

5-(2-Benzylsulfanyl-4-Cyclopropylamino-Pyrazolo-1,5-A][1,3,5]Triazin-8-YL)-Pentanenitrile (6A)

A solution of compound (5) and cyclopropylamine (1.2 g. 17.7 mmol) in anhydrous ethanol (10 mL) was stirred for 0.5 h at ambient temperature. The mixture was then diluted with EtOAc (200 mL), washed with saturated aqueous NaHCO3 and brine and dried over anhydrous Na2SO4. Removal of the solvent provided 5-(2-benzylsulfanyl-4-cyclopropylamino-pyrazolo[1,5-a][1,3,5]triazin-8-yl)-pentanenitrile (6) (4.3 g. 65% in two steps).

LCMS(API-ES) m/z: 378: 379 [M+H+].

Example 6

5-(4-Cyclopropylamino-2-Phenylmethanesulfonyl-methanesulfonyl-Pyrazolo[1,5-A][1,3,5]Triazin-8-YL)-Pentanenitrile (7A)

To a solution of compound (6a) (3.78 g, 10 mmol) in CH2Cl2 (200 mL) was added mCPBA (5.5 g, 22 mmol, 77%). The reaction mixture was stirred for 2 h and filtered. The filtrate was washed with saturated NaHCO3 followed by brine and dried over anhydrous Na2SO4. Removal of the solvent provided 5-(4-cyclopropylamino-2-phenylmethanesulfonyl-pyrazolo [1,5-all 1,3,5]triazin-8-yl)-pentanenitrile 7a as a solid (3.5 g, 85%).

LCMS(API-ES) m/z: 410.15. 411.0 [M+H+]; 409.0 [M−H+].

Example 7

5-[2-(3-Amino-Phenylamino)-4-Cyclopropylamino-Pyrazolo[1,5-A][1,3,5]Triazin-8-YLI-Pentanenitrile (8A)

A mixture of compound (7a) (0.41 g. 1 mmol), and benzene-1,3-diamine (2.16 g. 20 mmol) in 50 mL of AcOH was heated at 70° C. for 2 h. The mixture was then concentrated, and the residue neutralized with NaHCO3 and extracted with EtOAc. The acetate solution was then washed by citric acid (10%), followed by brine, dried over Na2 SO4 and concentrated to give 3-[2-(3-amino-phenylamino)-8-(4-cyano-butyl)-pyrazolo[1,5-a][1,3,5]triazin-4-ylamino]-benzoic acid ethyl ester (8) as a thick oil (0.22 g, 60%).

LCMS(API-ES) m/z: 362.2. 363.0 [M+H+]; 361.0 [M−H+].

Example 8

5-[2-(3-Amino-Phenylamino)-4-Cyclopropylamino-Pyrazolo[1,5-A][1,3,5]Triazin-8-YL]-Pentanoic Acid Methyl Ester (9A)

To a solution of compound (8a) (0.18 g. 0.5 mmol) in 30 mL of MeOH was bubbled through HCl gas at 0° C. for 5 mm. The reaction mixture was sealed and stirred at room temperature for 20 h. A mixture of ester and imine was obtained, which when brought to reflux for 2 h to give the methyl ester exclusively. The mixture was then concentrated and the residue was dissolved in EtOAc, washed with NaHCO3 followed by brine. The organic extract was dried, concentrated and purified by flash chromatography (CH2Cl2/EtOAc 2:1) to provide 5-[2-(3-amino-phenylamino)-4-cyclopropylamino-pyrazolo[1,5-a][1,3,5]triazin-8-yl]-pentanoic acid methyl ester 9a (0.13 g, 65%). LCMS(API-ES) m/z: 395.2. 396.0 [M+H+]; 394.0 [M−H+].

Example 9

5-[2-(3-Amino-Phenylamino)-4-Cyclopropylamino-Pyrazolo[1,5-A][1,3,5]Triazin-8-YI]-Pentanoic Acid (10A)

To a solution compound (9a) (0.12 g, 0.3 mmol) in 10 mL of MeOH and 0.5 mL of H2O was added NaOH (40 mg, 1 mmol). The reaction mixture was refluxed for 1 h, concentrated to re-move MeOH. The reaction solution was adjusted to pH 4 with HCl and the solid was collected by filtration, washed with water, and dried in vacuum over P2O5 to give 5-[2-(3-amino-phenylamino)-4-cyclopropylamino-pyrazolo[1,5-a][1,3,5]triazin-8-yl]-pentanoic acid (10a) (0.1 g, 90%).

LCMS(API-ES) m/z: 381.2, 382.0 [M+H+]; 380.0 [M−H+].

Example 10

(11,14)3,5-N-{Cyclopropyl-Pyrazolo[1,5-A][1,3,5]Triazin-4-YL-Amino}-(2N,4N)-Phenyl-1,5-Diaza-Cyclotetradeca-8-One (11A)

A solution of compound (10a) (0.1 g, 0.25 mmol) and HATU (0.12 g. 0.3 mmol) in 5% DIEA/NMP (1 mL) was stirred at room temperature for 30 min. (11.14)3,5N-{cyclopropyl-pyrazolo[1,5-a][1,3,5]triazin-4-yl-amino}-(2N,4N)-phenyl-1,5-diaza-cyclotetradeca-8-one (11a) was obtained by preparative RP-HPLC (0.05 g, 55%)

LCMS(API-ES) m/z: 363.1, 364.0 [M+H+]; 362.0 [M−H+].

In a manner similar to that recited in Examples 1-10, compounds having the following formulas were synthesized and purified.

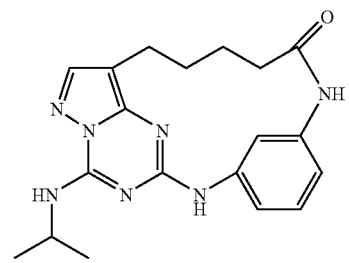

(11b)

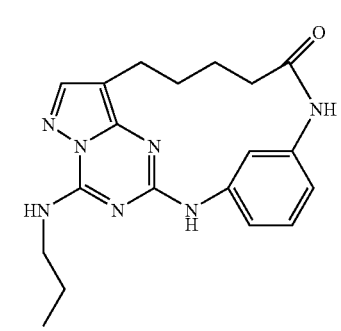

(11c)

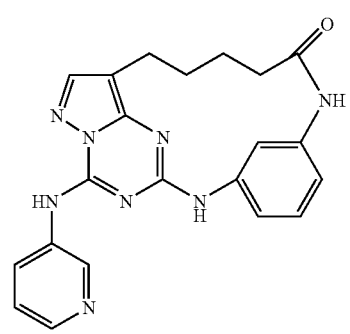

(11d)

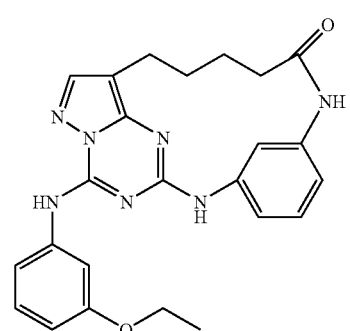

(11e)

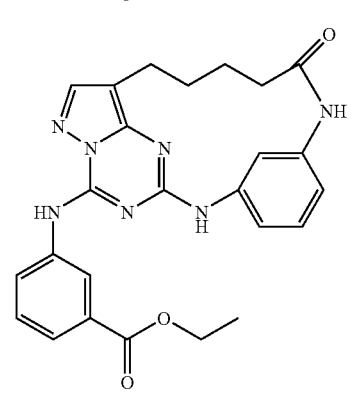

(11f)

Example 11

(11,14)3,5 N-{[{N-Methyl-N-(1-Mehyl-Pyrrolidin-3-YL)-Carbonyl}-Phen-3-YL]-Pyrazolo[1,5-A][1,3,5]Triazin-4-YL-Amino}-(2N,4N)-Phenyl-1,5-Diaza-Ccyclotetradeca-8-One (11G)

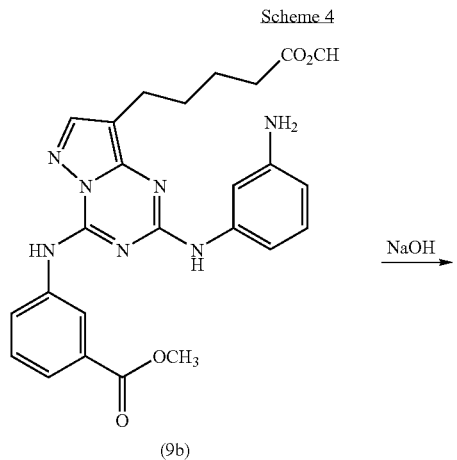

1,3-[2-(3-Amino-phenylamino)-8-(4-methoxycarbonyl-butyl)-pyrazolo[1,5-a][1,3,5]triazin-4-ylamino]-benzoic acid methyl ester (9b) was obtained in a similar manner to that recited in Example 8.

LCMS(API-ES) m/z: 489.5. 490.1 [M+H+]; 488.0 [M−H+].

Example 12

3-[2-(3-Amino-Phenylamino)-8-(4-Carboxy-Butyl)-Pyrazolo[1,5-A][1,3,5]Triazin-4-Ylamino]-Benzoic Acid (10 B)

To a solution of compound (9 b) (1.5 g, 3.06 mmol) in 50 mL of MeOH and 5 mL of H2O was added NaOH (400 mg. 10 mmol). The reaction mixture was refluxed for 1 h, and concentrated. Concentrated HCl was added to acidify the solution. The solid was collected by filtration, washed with water, and dried in vacuum over P2O5 to give 1,3-[2-(3-amino-phenylamino)-8-(4-methoxycarbonyl-butyl)-pyrazolo[1,5-a][1,3,5]triazin-4-ylamino]-benzoic acid methyl ester (13a) (1.3 g. 93%).

LCMS(API-ES) m/z: 461.4. 462.0 [M+H+]; 460.1 [M−H+].

Example 13

(11,14)3,5N-{[{N-Methyl-N-(1-Methyl-Pyrrolidin-3-YL)-Carbonyl}-Phen-3-YL]-Pyrazolo[1,5-A][1,3,5]Triazin-4-YL-Amino}-(2N,4N)-Phenyl-1,5-Diaza-Cyclotetradeca-8-One (11 G)

To a mixture of compound (10b) (300 mg, 0.6 mmol), DIEA (0.45 mL) in 60 mL of NMP was added HATU (410 mg, 1.08 mmol). The reaction mixture was sonicated for 5 min, and allowed to stand for 0.5 h at room temperature. Methyl-(1-methyl-pyrrolidin-3-yl)-amine (0.117 mL, 0.9 mmol) was added, followed by additional HATU (228 mg. 0.6 mmol). The reaction mixture was stirred at room temperature for 0.5 h. The crude product was purified by preparative RP-HPLC to yield (11,14)3,5N-{[{N-methyl-N-(1-methylpyrrolidin-3-yl)-carbonyl}-phen-3-yl]-pyrazolo[1,5-a][1,3,5]triazin-4-yl-amino}(2N,4N)-phenyl-1,5-diaza-cyclotetradeca-8-one (11g) (210 mg, 57%). LCMS(API-ES) m/z: 539.6. 540.2 [M+H+]; 538.1 [M−H+].

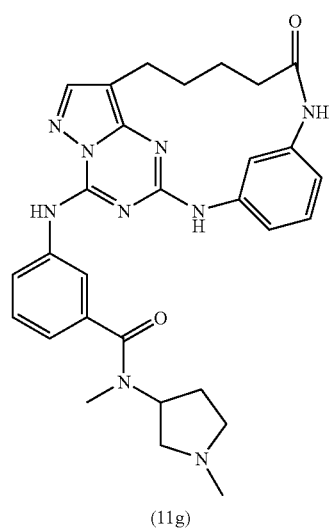

In a manner similar to that recited in the foregoing examples, compounds having the following formulas were synthesized and purified.

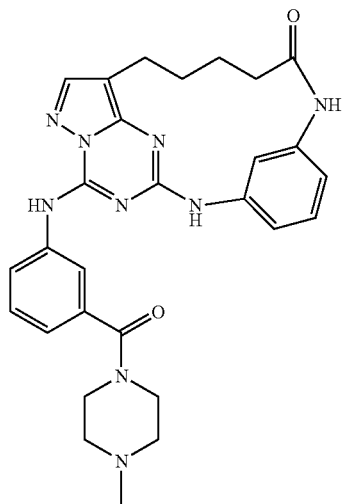
(11h)
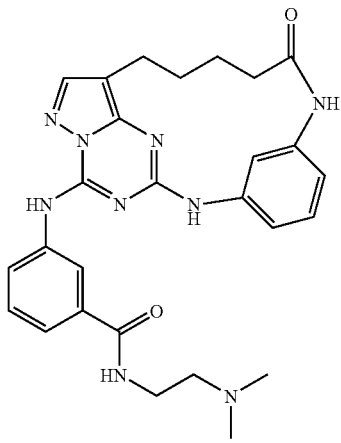
(11k)
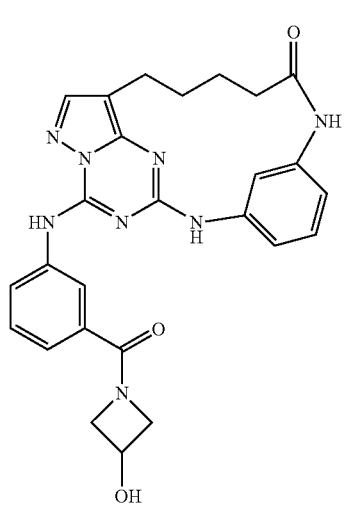
(11l)
(11i)
(11j)
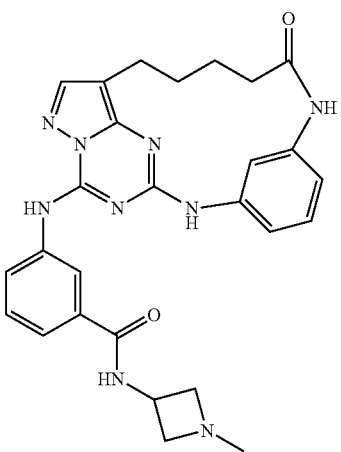
(11m)

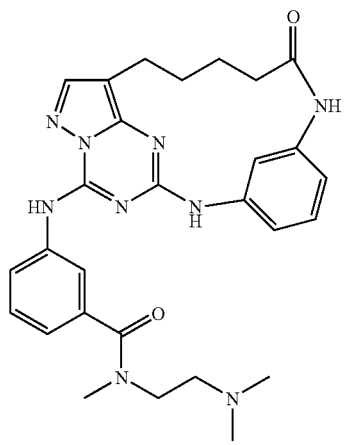
(11n)
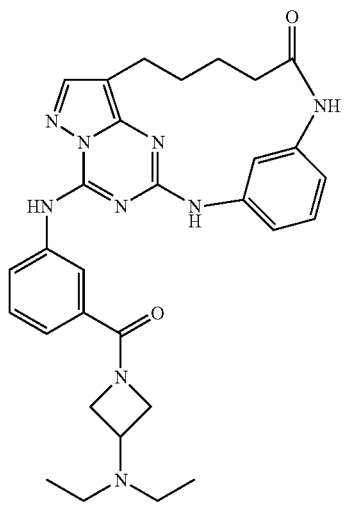
(11q)
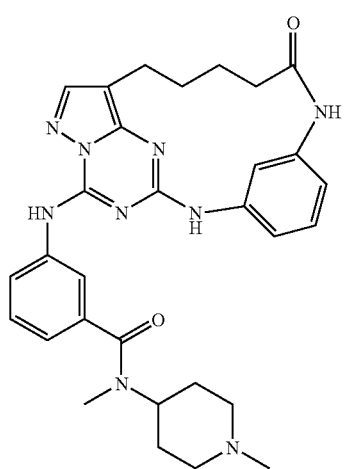
(11o)
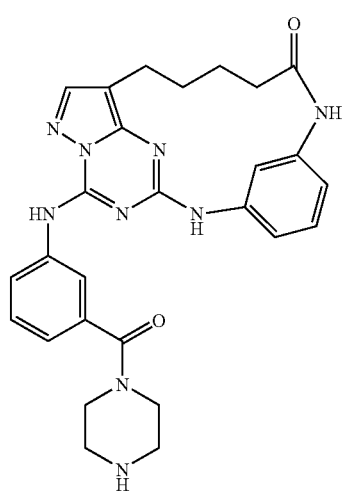
(11r)
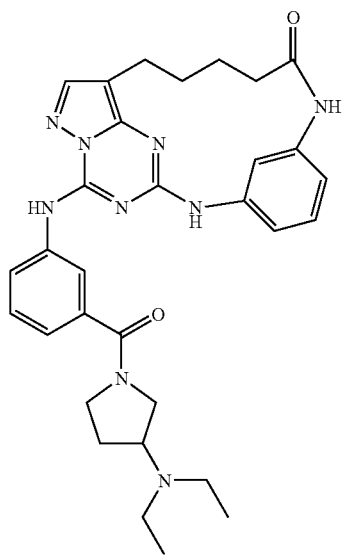
(11p)
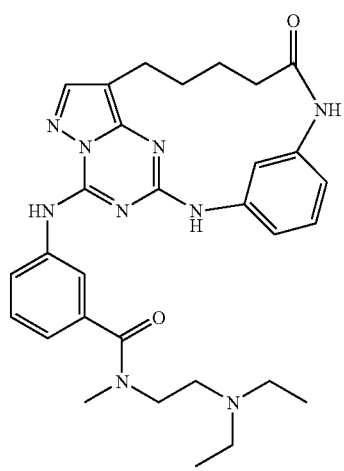
(11s)

Example 14
(11,14)3,5 N-{[(3-Dimethylamino-Pyrrolidine-1-Carbonyl)-Phen-3-YL]-Pyrazolo[1,5-A]Pyrimidin-2.4-YL-Diamino}-(2N,4N)-Phenyl-1,5-Diaza-Cyclotetradecan-6-One (18A)
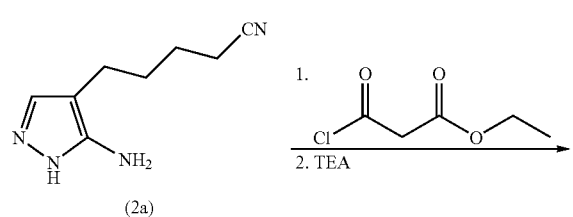
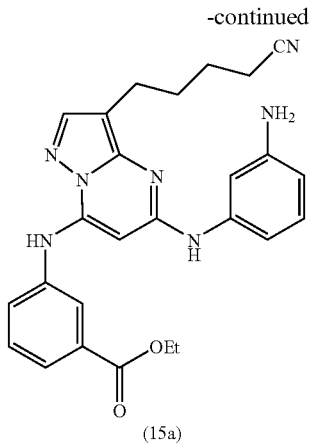
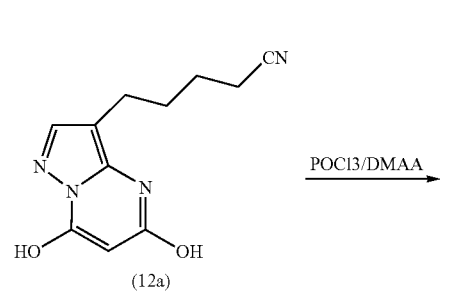
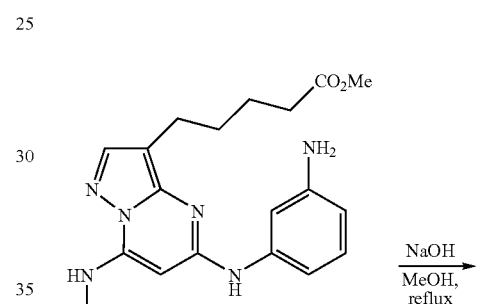
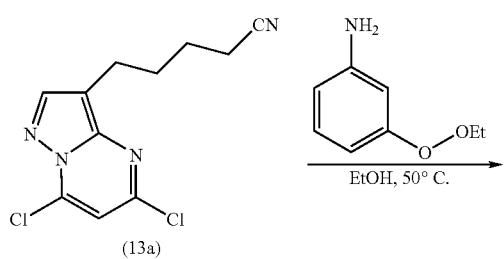
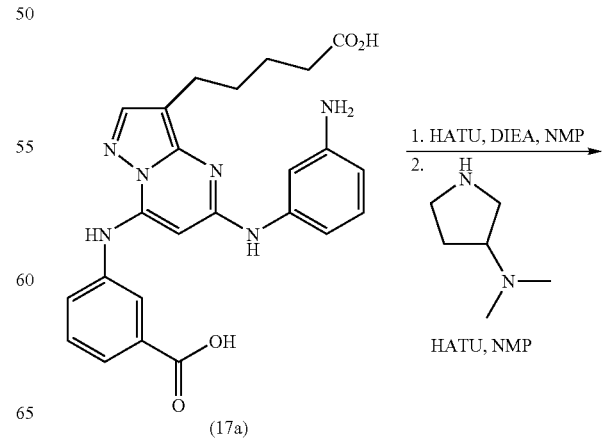

-continued

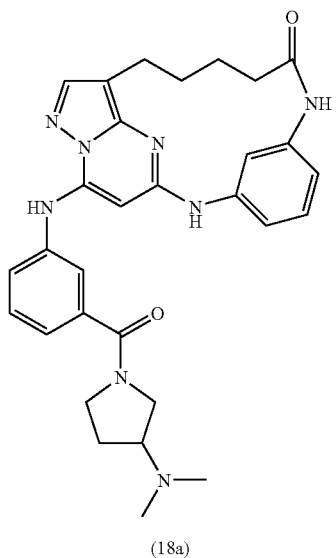

(18a)

Example 15

5-(5,7-Dihydroxy-Pyrazolo[1,5-A]Pyrimidin-3-YL)-Pentanenitrile (12 A)

To a solution of 5-(5-amino-1 H-pyrazol-4-yl)-pentanenitrile (2a) (1 g, 6.09 mmol) in 20 mL of EtOAc was added ethyl 3-chloro-3-oxopropionate (2.34 mL, 18.27 mmol) dropwise with stirring in a ice-water bath, followed by TEA (3.08 mL, 30.45 mmol). The reaction mixture was allowed to stir at room temperature for 2 h. The reaction mixture was diluted with EtOAc, washed by 10% aqueous HCl, saturated NaHCO3 and brine, dried over anhydrous Na2 SO4 and concentrated.

A solution of above residue in MeOH (10 mL) and TEA (2 mL) was refluxed for 2 h, concentrated and dried in vacuum to give 5-(5,7-dihydroxy-pyrazolo[1,5-a]pyrimidin-3-yl)-pentanenitrile (15), which was used without further purification in the next step (1.56 g).

LCMS(API-ES) m/z: 232.2. 233.0 [M+H+]; 231.0 [M−H+].

Example 16

5-(5,7-Dichloro-Pyrazolo[1,5-A]Pyrimidin-3-YL)-Pentanenitrile (13A)

A mixture of compound (12a) (1.56 g. 6.74 mmol) and N,N-dimethylaniline (854 μl, 6.74 mmol) in phosphorus oxychloride (25 mL) was heated to reflux in a sealed tube for 4 h and then concentrated. The residue was dissolved in EtOAc (50 mL) and washed with saturated aq NaHCO3, 10% HCl, and brine and dried over anhydrous Na2 SO4. Removal of the solvent provided 5-(5,7-dichloro-pyrazolo[1,5-a]pyrimidin-3-yl)-pentanenitrile (13a). (1.24 g, 69%). LCMS(API-ES) m/z: 269.1, 269.0. 271.0 [M+H+].

Example 17

3-[5-Chloro-3-(4-Cyano-Bityl)-Pyrazolo[1,5-A]Pyrimidin-7-Ylamino]-Benzoic Acid Ethyl Ester (14A)

To a solution of compound (13a) (1.24 g, 4.62 mmol) in 10 mL of ethanol was added ethyl 3-aminobenzoate (764 mg. 4.62 mmol). The reaction mixture was heated at 50° C. for 2 h and then cooled to room temperature. Solvent was removed and the residue was dissolved in EtOAc (50 mL) and washed with saturated aq NaHCO3, 10% HCl, and brine and dried over anhydrous Na2 SO4. Removal of the solvent provided a residue that was purified by flash column with use of EtOAc/hexane (25% to 50%) to yield 3-[5-chloro-3-(4-cyano-butyl)-pyrazolo[1,5-a]pyrimidin-7-ylamino]-benzoic acid ethyl ester (14a) (1.0 g. 50%).

LCMS(API-ES) m/z: 397.8. 398.0. 400.0 [M+H+]; 395.9. 398.0 [M−H+].

Example 18

3-[5-(3-Amino-Phenylamino)-3-(4-Cyano-Butyl)-Pyrazolo[1,5-A]Pyrimidin-7-Ylamino]-Benzoic Acid Ethyl Ester (15A)

A mixture of compound (14a) (0.63 g. 1.6 mmol) and benzene-1,3-diamine (69 mg, 0.636 mmol) in 2 mL of NMP was heated at 160° C. overnight. The reaction mixture was diluted with EtOAc (50 mL) and washed with saturated aq NaHCO3 and brine and dried over anhydrous Na2 SO4. HPLC purification provided 3-[5-(3-amino-phenylamino)-3-(4-cyano-butyl)-pyrazolo[1,5-a]pyrimidin-7-ylamino]-benzoic acid ethyl ester (15a) (0.37 g. 50%).

LCMS(API-ES) m/z: 469.5, 470.1 [M+H+]; 468.0 [M−H+].

Example 19

3-[5-(3-Amino-Phenylamino)-3-(4-Methoxycarbonyl-Butyl)-Pyrazolo[1,5-A]Pyrimidin-7-Ylamino]-Benzoic Acid Methyl Ester (16A)

Through a solution of compound (15a) (0.24 g. 0.5 mmol) in 5 mL of MeOH was bubbled HCl gas at 0° C. for 5 min. The reaction mixture was sealed and stirred at room temperature for 1 h, concentrated, and the residue dissolved in EtOAc, washed with NaHCO3, brine and water. Organic extract was dried, concentrated to provide 3-[5-(3-amino-phenylamino)-3-(4-methoxycarbonyl-butyl)-pyrazolo[1,5-a]pyrimidin-7-ylamino]-benzoic acid methyl ester (16a) (102.1 mg).

LCMS(API-ES) m/z: 488.5, 489.1 [M+H+]; 487.0 [M−H+].

Example 20

3-[5-(3-Amino-Phenylamino)-3-(4-Carboxy-Butyl)-Pyrazolo[1,5-A]Pyrimidin-7-Ylamino]-Benzoic Acid (17A)

To a solution of compound (16a) (102.1 mg, 0.203 mmol) in 5 mL of MeOH was added 1 M NaOH (0.41 mL, 0.407 mmol). The reaction mixture was refluxed for 1 h, and concentrated. HPLC purification gave 3-[5-(3-amino-phenylamino)-3-(4-carboxy-butyl)-pyrazolo[1,5-a]pyrimidin-7-ylamino]-benzoic acid (17a) (50 mg).

LCMS(API-ES) m/z: 460.5. 461.1 [M+H+]; 459.0 [M−H+].

Example 21

(11,14)3,5N-{[(3-Dimethylamino-Pyrrolidine-1-Carbonyl)-Phen-3-YL]-Pyrazolo[1,5-A]Pyrimidin-2, 4-YL-Diamino}-(2N,4N)-Phenyl-1,5-Diaza-Cyclotetradecan-6-One (18A)

To a mixture of compound (17 a) (35 mg, 0.075 mmol), DIEA (50 μL) in 1 mL of NMP was added HATU (50 mg, 0.12 mmol). The reaction mixture was sonicated for 2 min, and allowed to stand for 0.5 h at room temperature After which, dimethyl-pyrrolidin-3-yl-amine (15 μL. 0.1 mmol) was added, followed by additional HATU (5 mg. 0.12 mmol). The reaction mixture was stirred at room temperature for 0.5 h. Preparative RP-HPLC purification provided (11,14)3,5N-{[(3-dimethylamino-pyrrolidine-1-carbonyl)-phen-3-yl]pyrazolo[1,5-a]pyrimidin-2,4-yl-diamino}-(2N,4N)-phenyl-1,5-diaza-cyclotetradecan-6-one (18a) (15 mg).

LCMS(API-ES) m/z: 538.6, 539.2 [M+H+]; 537.0 [M−H+].

In a similar manner, the following compound.

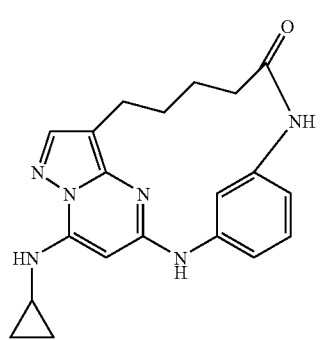

(18b)

was synthesized and purified.

Example 22

CK2 Protein Kinase Inhibition Assay

CK2 protein kinase activity was measured through use of a spectrophotometric PK/LDH coupled assay to detect ATP turnover. Full Length His-tagged Human CK2 was cloned, expressed, and purified from an *E. coli* expression system. The peptide substrate for CK2 phosphorylation was RRRD-DDSDDD (Genscript Corporation, Piscataway, N.J., USA). A typical CK2 enzymatic assay contained ~20 nM human CK2, 100 μM peptide substrate, 50 mM Tris-HCl pH 8.0, 100 mM NaCl, 10 mM MgCl2, 200 μM EDTA, 5 mM 2-mercaptoethanol, 1 mM phosphoenol pyruvate, 150 μM NADH, 0.5% PK/LDH Mix (Sigma #P-0294), 2.5% DMSO and 50 μM ATP. Inhibitor compounds were suspended in 100% DMSO and added to achieve various concentrations at a constant DMSO proportion of 2.5% by volume. Prior to the addition of ATP to initiate the phosphorylation reaction, CK2 enzyme was pre-incubated with inhibitors and other assay components for 5 min. Progress of the reaction was continuously monitored by the change in UV/Vis absorbance at 340 nm. Reaction rates were plotted versus inhibitor concentration and Ki values were fitted with the assumption of competitive inhibition and use of a Km value of 10 μM. In the case of very potent binding, tight-binding methods were employed to determine Ki. The results are recorded in Tables 1 and 2.

Example 23

Inhibition of Cell Growth

HCT-116 and PC-3 cells were cultured at 37° C. with 5% $CO_2$ and in 10% fetal bovine serum with McCoy's 5A modified medium and F-12 K medium respectively. Cells were plated on 96 well plates at a density of 2,000-4,000/well in the volume of 100 μL medium. After overnight incubation, 50 μL more medium containing various amount of CK2 inhibitors were added into each well to give final inhibitor concentrations ranging from 0.01 to 20 μM in 1% dimethylsulfoxide. The control wells contained 1% dimethylsulfoxide only in their medium. After further incubation of three to five days to allow cells grow before the control cells reach confluence, 15 μL/well MTT reagent (5 mg/mL) were added and incubated for 4 h. After the incubation, the medium was removed and the newly generated formazan solubilized with dimethylsulfoxide (100 μL/well) and measured at 540 nm. The absorption data were fit into equation and calculated for IC50 values through use of the program KaleidaGraph (Synergy Software). The fitting equation for IC50 is $y=a+b/(1+(x/IC50))$; x is the compound concentration, a is the background absorption at 540 nM, and b is the absorption at zero compound concentration. The results are recorded in Tables 1 and 2.

TABLE 1

Triazine-based compounds.

(11)

| Compound | Name | $K_i$ (μM) | IC$_{50}$ HCT 116 cells (μM) | IC$_{50}$ PC-3 (μM) |
|---|---|---|---|---|
| 11a | (11,14)3,5N-{cyclopropyl-pyrazolo[1,5-a][1,3,5]triazin-4-yl amino}-(2N,4N)-phenyl-1,5-diaza-cyclotetradeca-8-one | <0.1 | <1 | <1 |
| 11b | (11,14)3,5N-{iso-propyl-pyrazolo[1,5-a][1,3,5]triazin-4-yl-amino}-(2N,4N)-phenyl-1,5-diaza-cyclotetradeca-8-one | | | |
| 11c | (11,14)3,5N-{n-propyl-pyrazolo[1,5-a][1,3,5]triazin-4-yl-amino}-(2N,4N)-phenyl-1,5-diaza-cyclotetradeca-8-one | | | |
| 11d | (11,14)3,5N-{pyrid-3-yl-pyrazolo[1,5-a][1,3,5]triazin-4-yl-amino}-(2N,4N)-phenyl-1,5-diaza-cyclotetradeca-8-one | <0.1 | <1 | <1 |
| 11e | (11,14)3,5N-{(3-ethoxyphenyl)-pyrazolo[1,5-a][1,3,5]triazin-4-yl-amino}-(2N,4N)-phenyl-1,5-diaza-cyclotetradeca-8-one | <0.1 | <1 | <1 |
| 11f | (11,14)3,5N-{(3-ethoxycarbonylphenyl)-pyrazolo[1,5-a][1,3,5]triazin-4-yl-amino}-(2N,4N)-phenyl-1,5-diaza-cyclotetradeca-8-one | | | |

TABLE 1-continued

Triazine-based compounds.

(11)

| Compound | Name | $K_i$ (μM) | IC$_{50}$ HCT 116 cells (μM) | IC$_{50}$ PC-3 (μM) |
|---|---|---|---|---|
| 11g | (11,14)3,5N-{3-(3-{[methyl(1-methylpyrrolidin-3-yl)amino]carbonyl}phenyl)-pyrazolo[1,5-a][1,3,5]triazin-4-yl-amino}-(2N,4N)-phenyl-1,5-diaza-cyclotetradeca-8-one | <0.1 | <1 | <1 |
| 11h | (11,14)3,5N-{3-(4-methylpiperazin-1-ylcarbonyl)phenyl-pyrazolo[1,5-a][1,3,5]triazin-4-yl-amino}-(2N,4N)-phenyl-1,5-diaza-cyclotetradeca-8-one | <0.1 | <1 | <1 |
| 11i | (11,14)3,5N-{[3-(dimethylamino)pyrrolidin-1-yl]carbonyl}phenyl-pyrazolo[1,5-a][1,3,5]triazin-4-yl-amino}-(2N,4N)-phenyl-1,5-diaza-cyclotetradeca-8-one | <0.1 | <1 | <1 |
| 11j | (11,14)3,5N-{4-[(3-{3-(diethylamino)carbonyl}phenyl]amino}-pyrazolo[1,5-a][1,3,5]triazin-4-yl-amino}-(2N,4N)-phenyl-1,5-diaza-cyclotetradeca-8-one | <0.1 | <1 | <1 |
| 11k | (11,14)3,5N-{4-{[3-({2-(dimethylamino)ethyl]-amino}carbonyl)phenyl]amino}-pyrazolo[1,5-a][1,3,5]triazin-4-yl-amino}-(2N,4N)-phenyl-1,5-diaza-cyclotetradeca-8-one | <0.1 | <1 | <1 |
| 11l | (11,14)3,5N-{4-({3-[(3-hydroxyazetidin-1-yl)carbonyl]phenyl}amino)-pyrazolo[1,5-a][1,3,5]triazin-4-yl-amino}-(2N,4N)-phenyl-1,5-diaza-cyclotetradeca-8-one | <0.1 | <1 | <1 |
| 11m | (11,14)3,5N-{{[(1-methylazetidin-3-yl)amino]carbonyl}phenyl)amino]-pyrazolo[1,5-a][1,3,5]triazin-4-yl-amino}-(2N,4N)-phenyl-1,5-diaza-cyclotetradeca-8-one | <0.1 | <1 | <1 |
| 11n | (11,14)3,5N-{4-[(3-{[[2-(dimethylamino)ethyl](methyl)-amino]carbonyl}phenyl)amino]-pyrazolo[1,5-a][1,3,5]triazin-4-yl-amino}-(2N,4N)-phenyl-1,5-diaza-cyclotetradeca-8-one | <0.1 | <1 | <1 |
| 11o | (11,14)3,5N-{4-{3-{[methyl(1-methylpiperidin-4-yl)amino]carbonyl}-phenyl)amino]-pyrazolo[1,5-a][1,3,5]triazin-4-yl-amino}-(2N,4N)-phenyl-1,5-diaza-cyclotetradeca-8-one | <0.1 | <1 | |
| 11p | (11,14)3,5N-{[(3-{[3-(diethylamino)pyrrolidin-1-yl]carbonyl}phenyl)amino]-pyrazolo[1,5-a][1,3,5]triazin-4-yl-amino}-(2N,4N)-phenyl-1,5-diaza-cyclotetradeca-8-one | <0.1 | <1 | <1 |
| 11q | (11,14)3,5N-{[(3-{[3-(diethylamino)azetidin-1-yl]carbonyl}-phenyl)amino]-pyrazolo[1,5-a][1,3,5]triazin-4-yl-amino}-(2N,4N)-phenyl-1,5-diaza-cyclotetradeca-8-one | <0.1 | <1 | <1 |
| 11r | (11,14)3,5N-{{[3-(piperazin-1-ylcarbonyl)phenyl]amino}-pyrazolo[1,5-a][1,3,5]triazin-4-yl-amino}-(2N,4N)-phenyl-1,5-diaza-cyclotetradeca-8-one | <0.1 | <1 | |
| 11s | (11,14)3,5N-{4-[(3-{[2-(diethylamino)ethyl](methyl)amino]-carbonyl}phenyl)amino]-pyrazolo[1,5-a][1,3,5]triazin-4-yl-amino}-(2N,4N)-phenyl-1,5-diaza-cyclotetradeca-8-one | <0.1 | <1 | |

TABLE 2

Pyrimidine-based compounds (18)

| Compound | Name | $K_i$ (μM) | IC$_{50}$ HCT 116 cells (μM) | IC$_{50}$ PC-3 (μM) |
|---|---|---|---|---|
| 18a | (11,14)3,5N-{[(3-Dimethylamino-pyrrolidine-1-carbonyl)-phen-3-yl]-pyrazolo[1,5-a]pyrimidin-2,4-yl-diamino}-(2N,4N)-phenyl-1,5-diaza-cyclotetradecan-6-one | <0.1 | <3 | <3 |
| 18b | (11,14)3,5N-{[(3-cyclopropyl)-pyrazolo[1,5-a]pyrimidin-2,4-yl-diamino}-(2N,4N)-phenyl-1,5-diaza-cyclotetradecan-6-one | <0.1 | <3 | <3 |

The examples above exemplify compounds of Formula (I) and assays that may readily be per-formed to determine their activity levels against CK2 protein kinase. It will be apparent that such assays to other suitable assays known in the art may be used to select an inhibitor having a desired level of activity against a selected target.

While the invention has been illustrated by reference to specific and preferred embodiments, those skilled in the art will recognize that variations and modifications may be made through routine experimentation and practice of the inventions.

What is claimed:

1. A compound having the structure

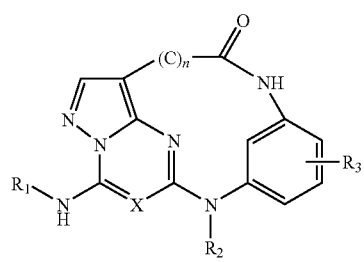

wherein
R1 is optionally substituted alkyl, alkenyl, alkynyl, cycloalkyl, aryl, or heteroaryl,
R2 is hydrogen, alkyl, alkenyl, alkynyl, aryl, or heteroaryl,
each R3 is, independently, hydrogen, optionally substituted alkyl, alkenyl, alkynyl, aryl, heteroaryl, or halo,
(C) is substituted alkyl, alkenyl, or aryl,
n=2-6; and
X is CH or N.

2. The compound of claim 1, wherein X is nitrogen.

3. The compound of claim 2, wherein R1 is C1-6 alkyl, C3-6 cycloalkyl, aryl, or heteroaryl groups.

4. The compound of claim 3, wherein R1 is optionally substituted cyclopropyl, i-Pr, or n-Pr.

5. The compound of claim 3, wherein R1 is phenyl.

6. The compound of claim 5, wherein the phenyl group has at least one substituent that is alkoxy, alkoxycarbonyl, or aminocarbonyl.

7. The compound of claim 6, wherein the alkoxy group is ethoxy.

8. The compound of claim 6, wherein the alkoxycarbonyl group is ethoxycarbonyl.

9. The compound of claim 3, wherein the heteroaryl group is pyridine.

10. The compound of claim 2, wherein the compound is selected from the group consisting of (11a)
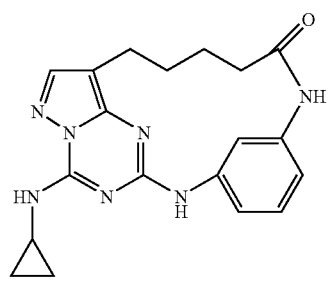

(11b)
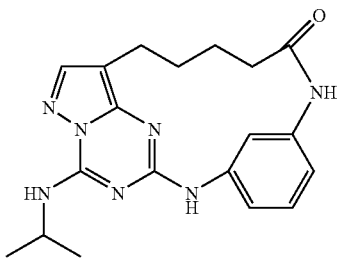

(11c)
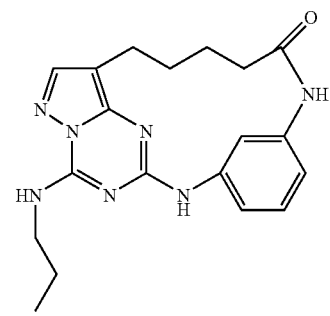

(11d)
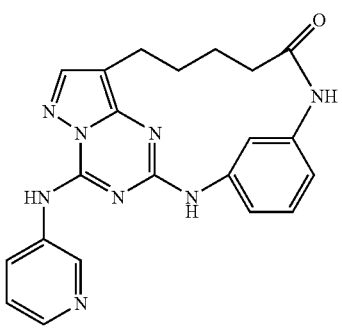

(11e)
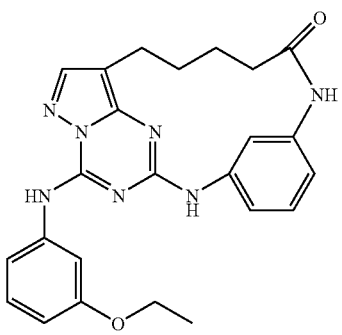

(11f)
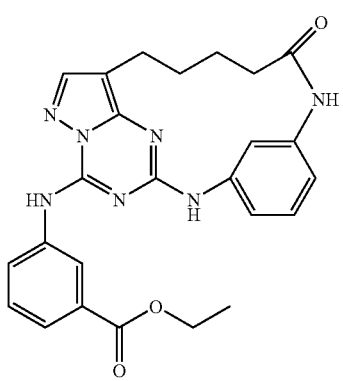

(11g)
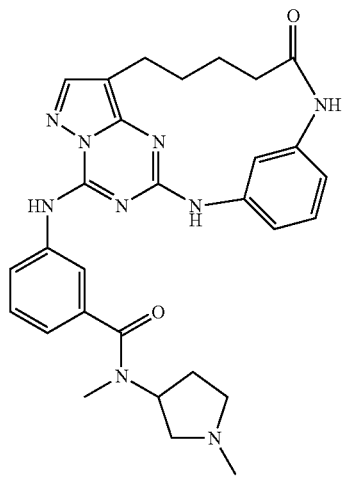
(11j)
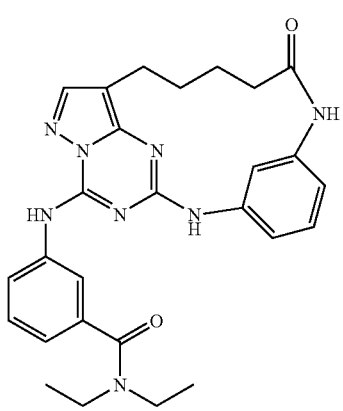
(11h)
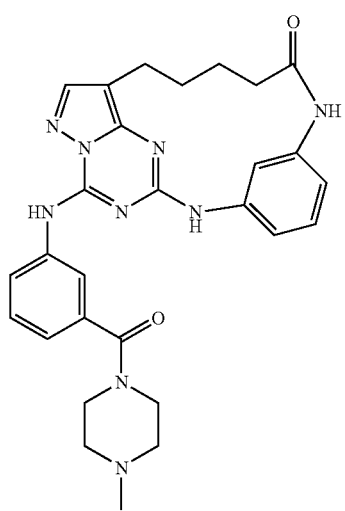
(11k)
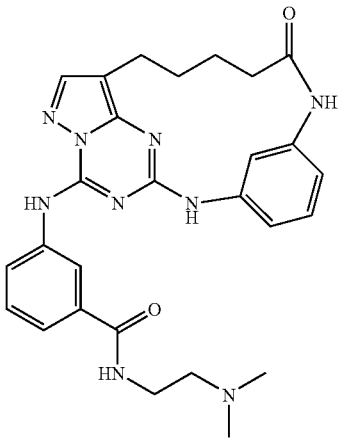
(11i)
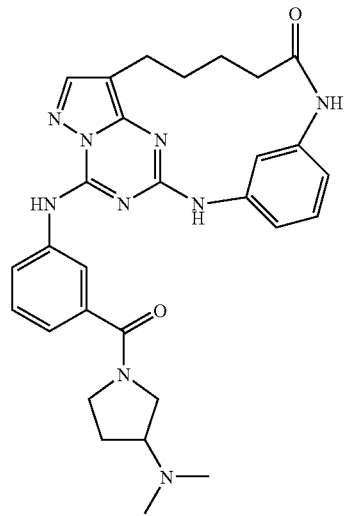
(11l)
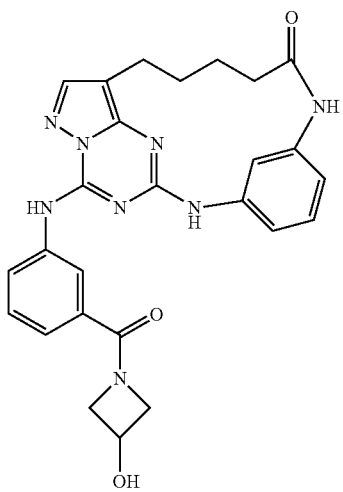

-continued
(11m)
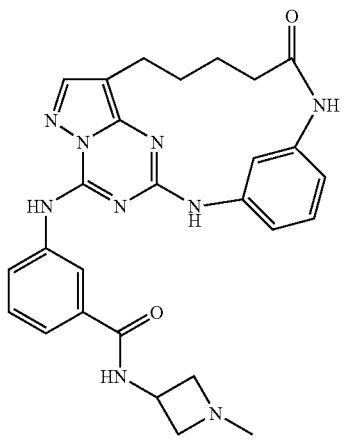
(11n)
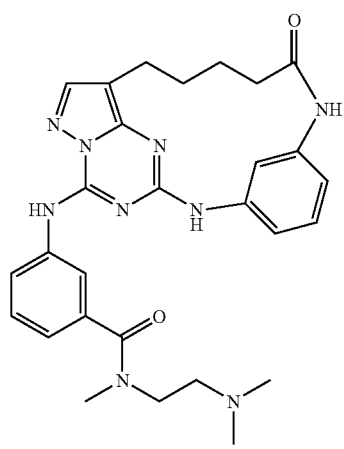
(11o)
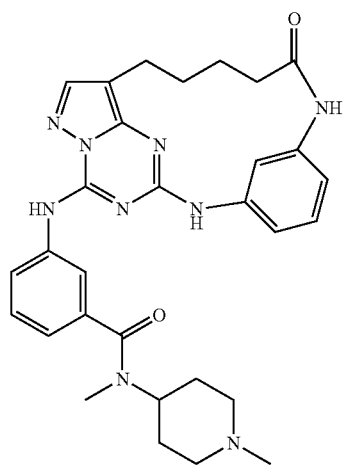
-continued
(11p)
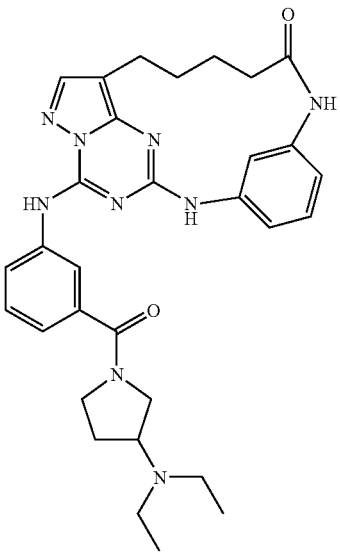
(11q)
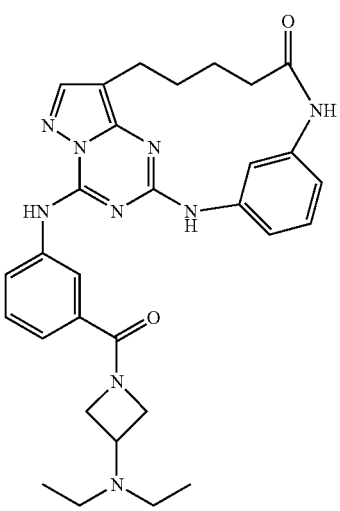
(11r)
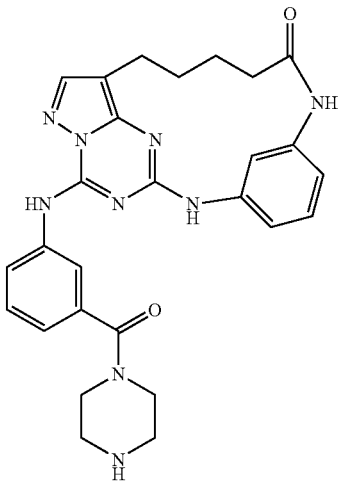

(11s)

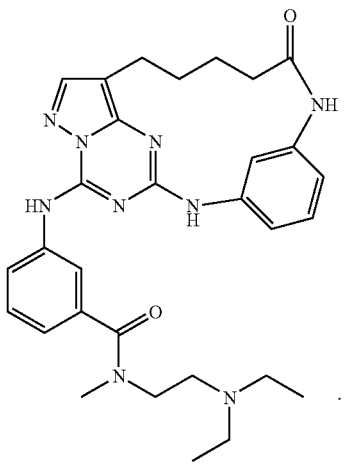

11. The compound of claim 1, wherein the compound is selected from the group consisting of
(11,14)3,5N-{cyclopropyl-pyrazolo[1,5-a][1,3,5]triazin-4-yl-amino}-(2N,4N)-phenyl-1,5-diaza-cyclotetradeca-8-one;
(11,14)3,5N-{isopropyl-pyrazolo[1,5-a][1,3.5]triazin-4-yl-amino}-(2N,4N)-phenyl-1,5-diaza- cyclotetradeca-8-one;
(11,14)3,5N-{n-propyl-pyrazolo[1.5-a][1,3,5]triazin-4-yl-amino}-(2N,4N)-phenyl-1,5-diaza- cyclotetradeca-8-one;
(11,14)3,5N-{pyrid-3-yl-pyrazolo[1,5-a][1,3,5]triazin-4-yl-amino}-(2N,4N)-phenyl-1,5- diaza-cyclotetradeca-8-one;
(11,14)3,5N-{(3-ethoxyphenyl)-pyrazolo[1,5-a][1,3,5] triazin-4-yl-amino}-(2N,4N)-phenyl- 1,5-diaza-cyclotetradeca-8-one;
(11,14)3,5N-{(3-ethoxycarbonylphenyl)-pyrazolo[1,5-a][1,3,5]triazin-4-yl-amino}-(2N,4N)- phenyl-1,5-diaza-cyclotetradeca-8-one;
(11,14)3,5N-{3-(3-{[methyl(1-methylpyrrolidin-3-yl)amino]carbonyl}phenyl)-pyrazolo[1,5- a][1,3,5]triazin-4-yl-amino}-(2N,4N)-phenyl-1,5-diaza-cyclotetradeca-8-one;
(11,14)3,5N-{3-(piperazin-1-ylcarbonyl)phenyl-pyrazolo[1,5-a][1,3,5]triazin-4-yl-amino}- (2N,4N)-phenyl-1,5-diaza-cyclotetradeca-8-one;
(11,14)3,5N-{3-[3-(dimethylamino)pyrrolidin-1-yl]carbonyl}phenyl-pyrazolo[1,5- a][1,3,5]triazin-4-yl-amino}-(2N,4N)-phenyl-1,5-diaza-cyclotetradeca-8-one;
(11,14)3,5N-{4-[(3-{[3-(dimethylamino)pyrrolidin-1-yl]carbonyl}phenyl)amino]- pyrazolo[1,5-a][1,3,5]triazin-4-yl-amino}-(2N,4N)-phenyl-1,5-diaza-cyclotetradeca-8-one;
(11,14)3,5N-{4-{[3-({[2-(dimethylamino)ethyl]amino}carbonyl)phenyl]amino}- pyrazolo[1,5-a][1,3,5]triazin-4-yl-amino}-(2N,4N)-phenyl-1,5-diaza-cyclotetradeca-8-one;
(11,14)3,5N-{4-({3-[(3-hydroxyazetidin-1-yl)carbonyl]phenyl}amino)-pyrazolo[1,5- a][1,3,5]triazin-4-yl-amino}-(2N,4N)-phenyl-1,5-diaza-cyclotetradeca-8-one;
(11,14)3,5N-{4-[(3-{[(3-hydroxycyclobutyl)amino]carbonyl}phenyl)amino]-pyrazolo[1,5- a][1,3,5]triazin-4-yl-amino}-(2N,4N)-phenyl-1,5-diaza-cyclotetradeca-8-one;
(11,14)3,5N-{4-[(3-{[[2-(dimethylamino)ethyl](methyl)amino]carbonyl}phenyl)amino]- pyrazolo[1,5-a][1,3,5]triazin-4-yl-amino}-(2N,4N)-phenyl-1,5-diaza-cyclotetradeca-8-one;
(11,14)3,5N-{4-[(3-{[methyl(1-methylpiperidin-4-yl)amino]carbonyl}phenyl)amino]- pyrazolo[1,5-a][1,3,5]triazin-4-yl-amino}-(2N,4N)-phenyl-1,5-diaza-cyclotetradeca-8-one;
(11,14)3,5N-{[(3-{[3-(diethylamino)pyrrolidin-1-yl]carbonyl}phenyl)amino]-pyrazolo[1,5- a][1,3,5]triazin-4-yl-amino}-(2N,4N)-phenyl-1,5-diaza-cyclotetradeca-8-one;
(11,14)3,5N-{[(3-{[3-(diethylamino)azetidin-1-yl]carbonyl}phenyl)amino]-pyrazolo[1,5- a][1,3,5]triazin-4-yl-amino}-(2N,4N)-phenyl-1,5-diaza-cyclotetradeca-8-one;
(11,14)3,5N-{{[3-(piperazin-1-ylcarbonyl)phenyl]amino}-pyrazolo[1,5-a][1,3,5]triazin-4-yl- amino}-(2N,4N)-phenyl-1,5-diaza-cyclotetradeca-8-one; and
(11,14)3,5N-{4-[(3-{[[2-(diethylamino)ethyl](methyl)amino]carbonyl}phenyl)amino]- pyrazolo[1,5-a][1,3,5]triazin-4-yl-amino}-(2N,4N)-phenyl-1,5-diaza-cyclotetradeca-8-one.

12. The compound of claim 1, wherein X is CH.
13. The compound of claim 12, wherein the compound is selected from the group consisting of (18a)

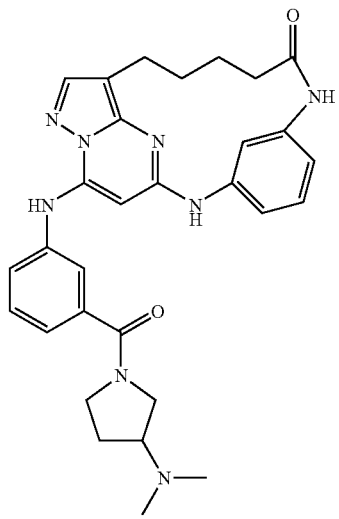

(18b)

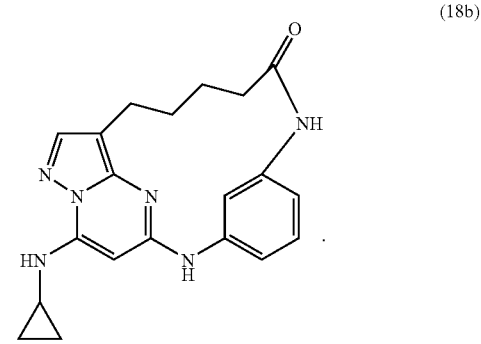

14. A pharmaceutical composition comprising at least one compound of claim 1 and one or more pharmaceutically acceptable carrier.

* * * * *